United States Patent
Wei et al.

(10) Patent No.: US 11,202,796 B2
(45) Date of Patent: *Dec. 21, 2021

(54) BRANCHED POLYETHYLENE GLYCOL EPOXY DERIVATIVE CROSSLINKED SODIUM HYALURONATE GEL, PREPARATION AND APPLICATION THEREOF

(71) Applicant: JENKEM TECHNOLOGY CO., LTD. (TIANJIN), Tianjin (CN)

(72) Inventors: Zhen Wei, Tianjin (CN); Meina Lin, Tianjin (CN); Xuan Zhao, Tianjin (CN)

(73) Assignee: JENKEM TECHNOLOGY CO., LTD. (TIANJIN), Tianjin (CN)

( * ) Notice: Subject to any disclaimer, the term of this patent is extended or adjusted under 35 U.S.C. 154(b) by 79 days.

This patent is subject to a terminal disclaimer.

(21) Appl. No.: 16/729,755

(22) Filed: Dec. 30, 2019

(65) Prior Publication Data
US 2020/0129542 A1   Apr. 30, 2020

Related U.S. Application Data

(63) Continuation of application No. PCT/CN2018/093133, filed on Jun. 27, 2018.

(30) Foreign Application Priority Data

Jun. 28, 2017 (CN) .......................... 201710507481.9
Jun. 22, 2018 (CN) .......................... 201810651800.8

(51) Int. Cl.
*A61K 31/728* (2006.01)
*C08B 37/08* (2006.01)
*C08J 3/24* (2006.01)

(52) U.S. Cl.
CPC ........ *A61K 31/728* (2013.01); *C08B 37/0072* (2013.01); *C08J 3/24* (2013.01)

(58) Field of Classification Search
None
See application file for complete search history.

(56) References Cited

FOREIGN PATENT DOCUMENTS

| CN | 106589424 A | * | 4/2017 | ............. A61L 27/20 |
|---|---|---|---|---|
| JP | 58038741 A | * | 3/1983 | ....... B32B 17/10761 |
| JP | 2015183145 A | * | 10/2015 | ............. C08G 59/20 |
| KR | 1020160035272 A | * | 3/2016 | ............. G03F 7/027 |

* cited by examiner

*Primary Examiner* — Dale R Miller
(74) *Attorney, Agent, or Firm* — Flener IP & Business Law; Zareefa B. Flener

(57) ABSTRACT

The present invention discloses a branched polyethylene glycol epoxy derivative crosslinked sodium hyaluronate gel, preparation and application thereof. The crosslinking agent used in the crosslinked sodium hyaluronate gel prepared by the present invention is a polyethylene glycol epoxy derivative, due to the existence of multiple ether bonds in the molecule of the crosslinking agent, there are more hydrogen bonds in the gel system; meanwhile, due to the particularity of the space structure of the branched polyethylene glycol epoxy derivative, the gel prepared has a more complex winding structure in its space, thus achieving better stability. Moreover, the branched polyethylene glycol epoxy derivative involved in the present invention is a compound with single molecular weight, therefore, the gel prepared thereby has better batch stability.

20 Claims, No Drawings

BRANCHED POLYETHYLENE GLYCOL EPOXY DERIVATIVE CROSSLINKED SODIUM HYALURONATE GEL, PREPARATION AND APPLICATION THEREOF

CROSS-REFERENCE TO RELATED APPLICATION

This application is a continuation application of International patent application No. PCT/CN2018/093133, filed on Jun. 27, 2018, which claims priority to Chinese patent application No. CN201810651800.8, filed on Jun. 22, 2018, and Chinese patent application No. CN201710507481.9, filed on Jun. 28, 2017. All of the aforementioned patent applications are hereby incorporated by reference in their entireties.

TECHNICAL FIELD

The present invention relates to the technical field of sodium hyaluronate gel, and in particular to a branched polyethylene glycol epoxy derivative crosslinked sodium hyaluronate gel, preparation and an application thereof.

BACKGROUND

Hyalouronic acid (HA) is a kind of linear viscous polysaccharide polymer formed by repeating disaccharide units of glucuronic acid and acetylglucosamine. Hyaluronic acid is a kind of endogenous substance in human body, it can be degraded by injecting hyaluronidase and is featured by good biocompatibility, high viscoelasticity and Non-Newtonian rheology character, zero toxicity, zero immunogenicity, no stimulation, high safety, etc., therefore, hyaluronic acid is widely used as a soft tissue filler in plastic surgery. Namely, hyaluronic acid is injected into skin to increase the volume of soft tissue, thus achieving wrinkle removal and shaping purpose. But due to its existence form, namely, a liquid form, hyaluronic acid is decomposed very easily in vivo under the action of hyaluronidase and free radicals, it is difficult to achieve shaping effect and maintain long duration of filling effect.

To overcome such a shortcoming, skilled persons have applied the means of crosslinking into hyaluronic acid, namely, hyaluronic acid molecules are linked together by a crosslinking agent to form a relatively stable net structure, so that hyaluronic acid cannot be easily decomposed anymore and maintains longer duration. After being modified by crosslinking, the sodium hyaluronate gel would have good viscoelastic property, high mechanical strength and long degradation time, and it is insoluble in water; meanwhile, crosslinking degree depends on physical property, thus conforming to cosmetic filling demands.

Currently, the crosslinking agent applied in the commercially available sodium hyaluronate products mainly includes: BDDE (butanediol diglycidyl ether and DVS (divinyl sulfone). The sodium hyaluronate gel cross-linked via BDDE is taken by Restylane series of Galderma, Juvederm series of Allergan, Stylage series of Laboratoires Vivacy and Hya-Dermis series; the sodium hyaluronate gel cross-linked via DVS is taken by Hylaform series of Genzyme, Varioderm series of Adoderm and Teosyal series of Teoxane. The gel prepared by the two crosslinking agents has rather different physical properties: DVS crosslinked product is hard and has high crosslinking activity; BDDE crosslinked product is soft and high expansion rate, moreover, the reaction is mild. It should be noted that the above crosslinking agent has toxicity or potential cancer risk, furthermore, the unreacted crosslinking agent may be wrapped by the crosslinked spatial net structure, therefore, resulting in high difficulty of removal.

The patent application CN201611246123.9 discloses an efficient and low-toxic crosslinking agent of polyethylene glycol epoxy derivative EPOX-O$\text{-}$($CH_2CH_2O$)$_n$EPOX (n=4, 5, 6, 7, 8, 9, 10, 11, 12 . . . 200), and the sodium hyaluronate gel prepared by the crosslinking agent has excellent performance. To further improve the in-vivo stability of gel, the present invention designs a branched polyethylene glycol epoxy derivative, as a crosslinking agent, the sodium hyaluronate gel prepared thereby has good softness, good viscoelasticity, low toxicity and product uniformity, furthermore, the gel has better stability.

SUMMARY

To overcome the disadvantages of the prior art, the present invention provides a branched polyethylene glycol epoxy derivative with a novel structure, a crosslinked gel and its preparation and an application thereof.

An aspect of the present invention provides a branched polyethylene glycol epoxy derivative, having the following structure:

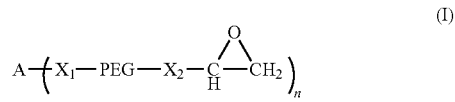

where, A is a core structure, namely, a polyol group, selected from: pentaerythritol, oligomeric pentaerythritol, glycerin, a residue of oligomeric glycerin and a glyceryl ether group, $X_1$ and $X_2$ are linking groups, independently selected from any one or a combination of two or more of the group consisting of: the above —$(CH_2)_i$—, —$(CH_2)_iO$—, —$(CH_2)_iCO$—, —$(CH_2)_iNH$—, —$(CH_2)_iNHCO(CH_2)_j$—, —$(CH_2)_iCONH(CH_2)_j$—, —$(CH_2)_iOCO(CH_2)_j$—, —$(CH_2)_iCOO(CH_2)_j$—,

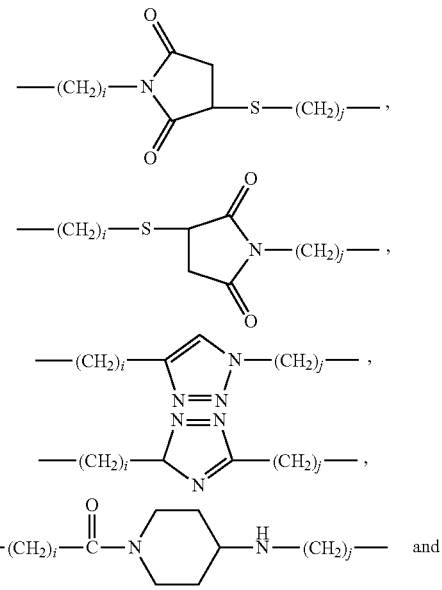

and

-continued

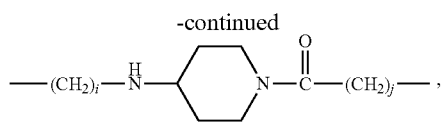

i and j are independently selected from an integer of 0-10,

PEG has the following structure: $-(CH_2CH_2O)_m-$, m is an integer of 4-200, n is an integer of 3-24, the branched polyethylene glycol epoxy derivative is a compound with single molecular weight.

In one embodiment of the present invention, the A has the following structure:

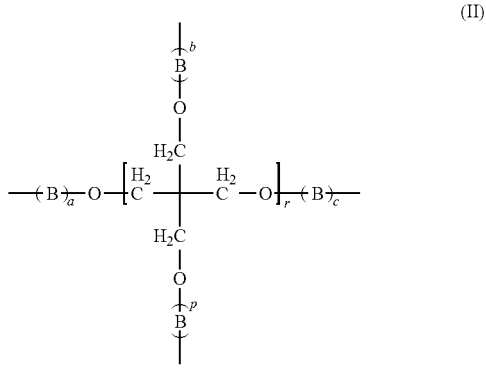

(II)

where, B has the following structure:

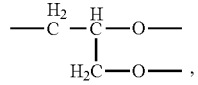

r is an integer of 1-5 (specifically 1, 2, 3, 4 or 5), a, b, c and d are integers, independently selected from 0 and 1, In a further embodiment of the present invention, the A has the following structure:

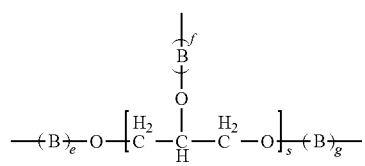

(III)

where, B has the following structure:

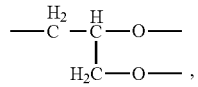

s is an integer of 1-5 (specifically 1, 2, 3, 4 or 5), e, f and g are integers, independently selected from 0 and 1.

In one embodiment of the present invention, the r is 1, 2 or 3 in the formula II.

In one embodiment of the present invention, the a, b, c and d are all 0 in the formula II.

In a further embodiment of the present invention, the a, b, c and d are all 1 in the formula II.

In one embodiment of the present invention, the s is 1, 2 or 3 in the formula III.

In one embodiment of the present invention, the e, f and g are all 0 in the formula III.

In a further embodiment of the present invention, the e, f and g are all 1 in the formula III.

In one embodiment of the present invention, the A has the following structure:

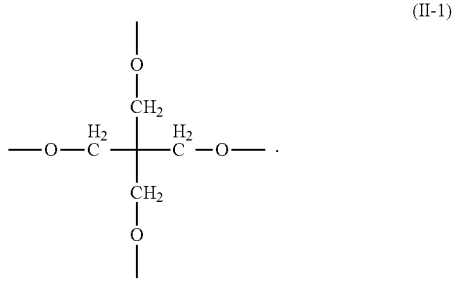

(II-1)

In one embodiment of the present invention, the A has the following structure:

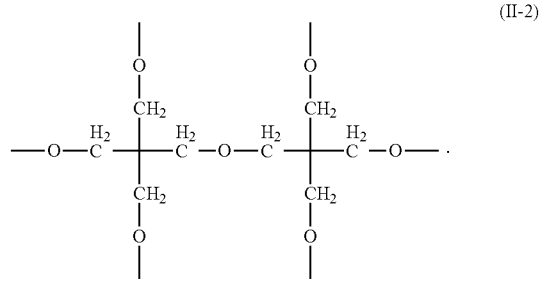

(II-2)

In one embodiment of the present invention the A has the following structure:

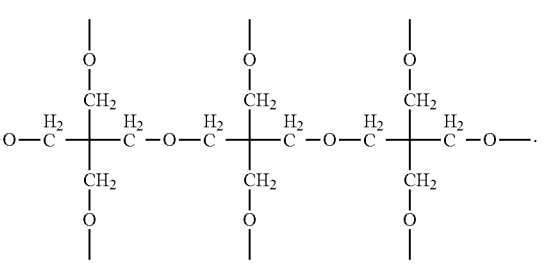

(II-3)

In one embodiment of the present invention, the A has the following structure:

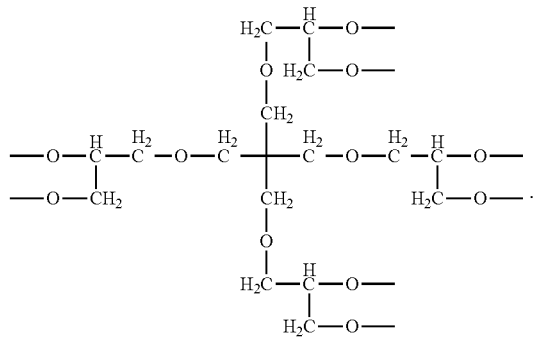

(II-4)

In one embodiment of the present invention, the A has the following structure:

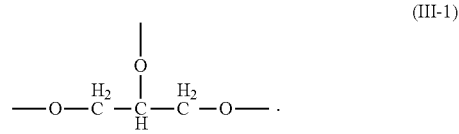

(III-1)

In one embodiment of the present invention, the A has the following structure:

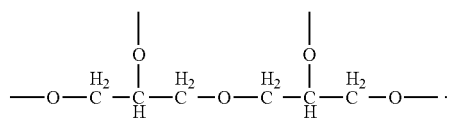

(III-2)

In one embodiment of the present invention, the n is an integer of 3-16, specifically, 3, 4, 5, 6, 7, 8, 10, 12, 14 or 16.

In one embodiment of the present invention, the i and j are independently selected from integers of 0-10 in X1, specifically, 0, 1, 2, 3, 4, 5, 6, 7, 8, 9 or 10, preferably 0, 1, 2 or 3.

In one embodiment of the present invention, the i and j are independently selected from integers of 0-10 in $X_2$, specifically, 0, 1, 2, 3, 4, 5, 6, 7, 8, 9 or 10, preferably 0, 1, 2 or 3.

In one embodiment of the present invention, the $X_1$ is selected from any one or a combination of two or more of the group consisting of: —$CH_2$—, —$CH_2CH_2$—, —$CH_2CH_2CH_2$—, —$CH_2CONH$—, —$CH_2CH_2CONH$—, —$CH_2CONHCH_2$—, —$CH_2CONHCH_2CH_2$—, —$CH_2CH_2CONHCH_2CH_2$—, —$CH_2CH_2NHCOCH_2$— and —$CH_2CH_2NHCOCH_2CH_2$—.

In a preferred embodiment of the present invention, the $X_1$ is —$CH_2CH_2CONH$—.

In one embodiment of the present invention, the $X_2$ is selected from any one or a combination of two or more of the group consisting of: —$CH_2$—, —$CH_2CH_2$—, —$CH_2CH_2CH_2$—, —$CH_2CONH$—, —$CH_2CH_2CONH$—, —$CH_2CONHCH_2$—, —$CH_2CONHCH_2CH_2$—, —$CH_2CH_2CONHCH_2CH_2$—, —$CH_2CH_2NHCOCH_2$— and —$CH_2CH_2NHCOCH_2CH_2$—.

In a preferred embodiment of the present invention, the $X_2$ is —$CH_2$—.

In the branched polyethylene glycol epoxy derivative of the present invention, m is an integer of 4-200, e.g., an integer of 4-100 (specifically, 4, 5, 6, 7, 8, 9, 10, 11, 12, 13, 14, 15, 16, 17, 18, 19, 20, 21, 22, 23, 24, 25, 30, 35, 40, 45, 50, 60, 70, 80, 90 or 100), an integer of 100-200 (specifically, 100, 110, 120, 130, 140, 150, 160, 170, 180, 190 or 200), preferably an integer of 4-100.

In a preferred embodiment of the present invention, the m is 4, 12 or 24.

In a preferred embodiment of the present invention, the branched polyethylene glycol epoxy derivative has the following structure:

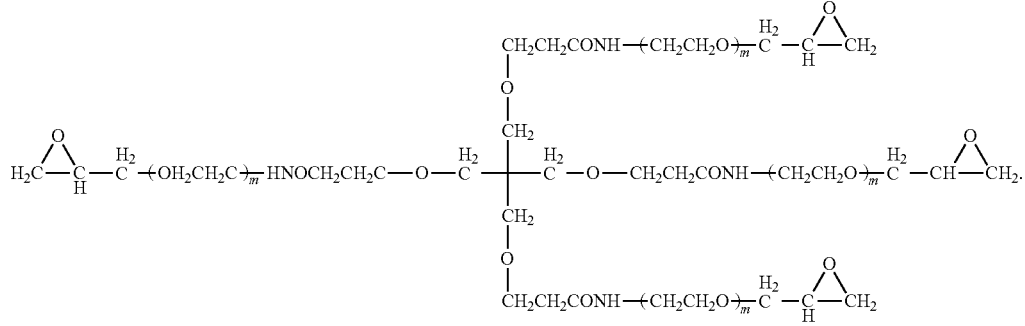

(I-1)

In one embodiment of the present invention, m is 4 in the formula I-1.

In one embodiment of the present invention, m is 12 in the formula I-1.

In one embodiment of the present invention, m is 24 in the formula I-1.

In a preferred embodiment of the present invention, the branched polyethylene glycol epoxy derivative has the following structure:

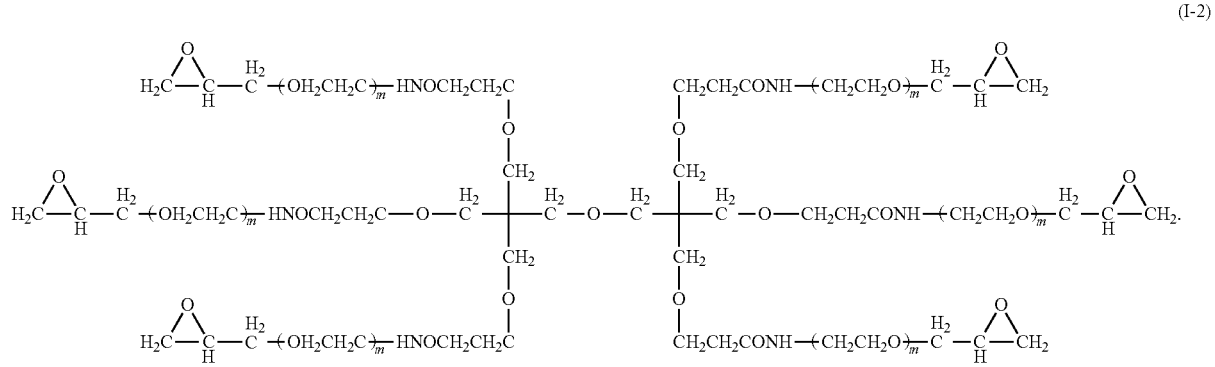

(I-2)

In one embodiment of the present invention, m is 4 in the formula I-2.

In one embodiment of the present invention, m is 12 in the formula I-2.

In one embodiment of the present invention, m is 24 in the formula I-2.

In a preferred embodiment of the present invention, the branched polyethylene glycol epoxy derivative has the following structure:

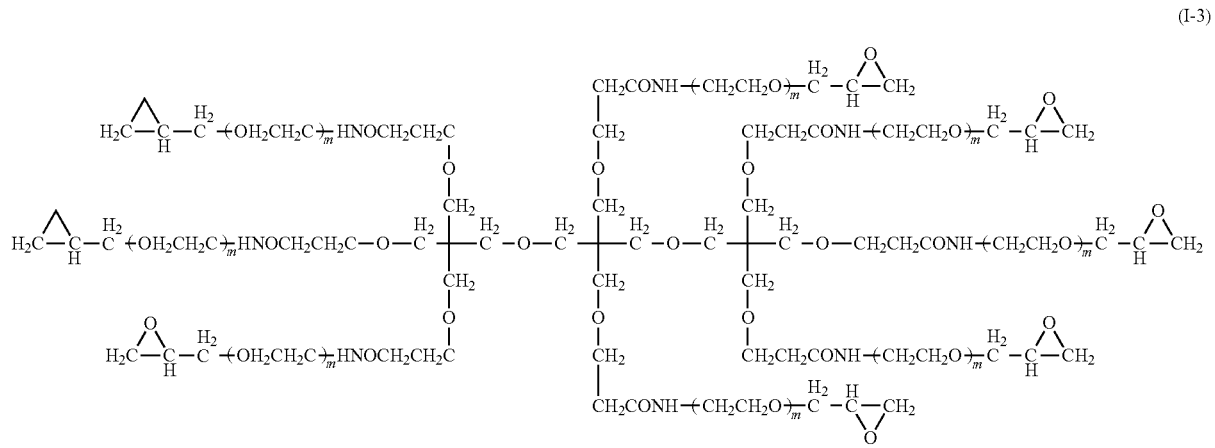

(I-3)

In one embodiment of the present invention, m is 4 in the formula I-3.

In one embodiment of the present invention, m is 12 in the formula I-3.

In one embodiment of the present invention, m is 24 in the formula I-3.

In a preferred embodiment of the present invention, the branched polyethylene glycol epoxy derivative has the following structure:

(I-4)

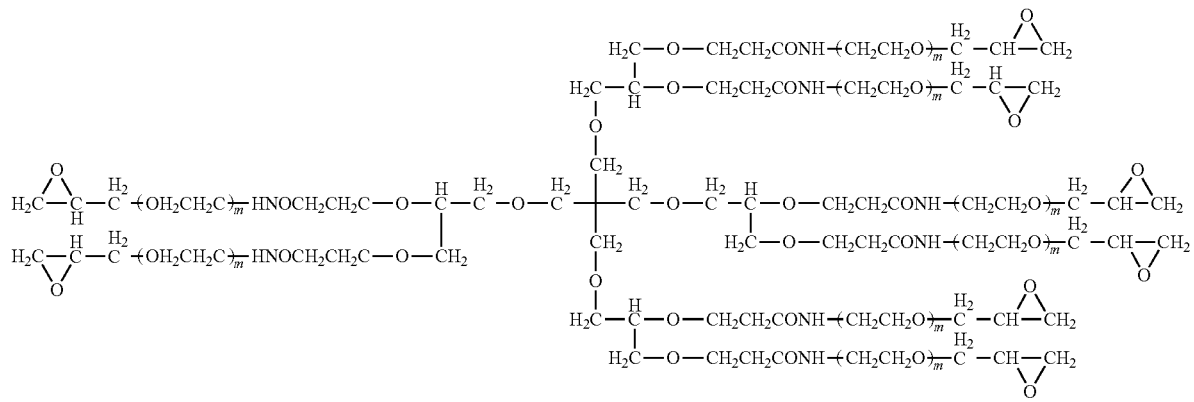

In one embodiment of the present invention, m is 4 in the formula I-4.

In one embodiment of the present invention, m is 12 in the formula I-4.

In one embodiment of the present invention, m is 24 in the formula I-4.

In a preferred embodiment of the present invention, the branched polyethylene glycol epoxy derivative has the following structure:

(I-5)

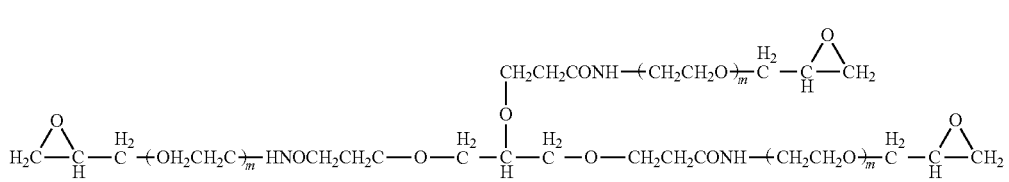

In one embodiment of the present invention, m is 4 in the formula I-5.

In one embodiment of the present invention, m is 12 in the formula I-5.

In one embodiment of the present invention, m is 24 in the formula I-5.

In a preferred embodiment of the present invention, the branched polyethylene glycol epoxy derivative has the following structure:

(I-6)

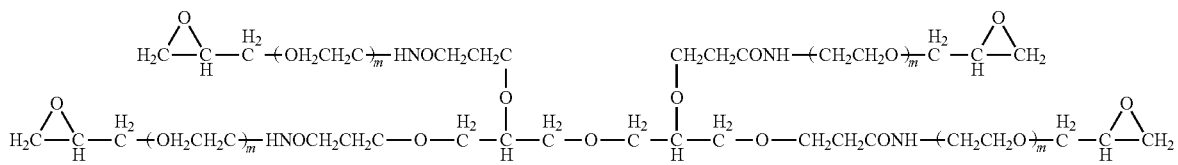

In one embodiment of the present invention, m is 4 in the formula I-6.

In one embodiment of the present invention, m is 12 in the formula I-6.

In one embodiment of the present invention, m is 24 in the formula I-6.

A further aspect of the present invention provides a preparation method of the above branched polyethylene glycol epoxy derivative, the method comprises a step of catalyzing

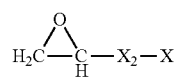

and branched polyethylene glycol $A\text{--}(X_1\text{-PEG-H})_n$ for reaction via a catalyst in solvent, where, the A, $X_1$, $X_2$, PEG and n are defined the same as the present invention, —X is a leaving group, the catalyst is a base catalyst, including organic base or inorganic base.

In one embodiment of the present invention, the solvent includes but not limited to: 1, 4-dioxane, tetrahydrofuran, toluene, acetone, ethyl acetate, acetonitrile, N, N-dimethylformamide, dimethyl sulfoxide or water.

In one embodiment of the present invention, the base catalyst is selected from but not limited to: one or more of pyridine, triethylamine, cesium carbonate, sodium carbonate, potassium carbonate, sodium bicarbonate, potassium bicarbonate, sodium hydroxide, potassium hydroxide, sodium alkoxide and potassium alkoxide.

In one embodiment of the present invention, the leaving group is selected from: one of

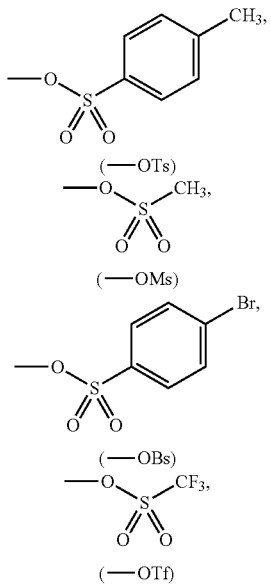

—F, —I, —Br and —Cl.

In one embodiment of the present invention, the molar ratio of each hydroxy in the branched polyethylene glycol to

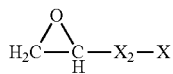

is 1:2-4.

In one embodiment of the present invention, the preparation method further includes purification step: specifically, the purification is by the means selected from any one or a combination of two or more of the group consisting of: rotary evaporation, washing, extraction, molecular distillation and column separation.

In a preferred embodiment of the present invention, the preparation method includes the following specific steps: the above branched polyethylene glycol, solvent and catalyst are added to a reaction vessel for stirring, halogenated or sulphonated epoxypropane is dropwise added to the above mixture, the reaction temperature was controlled within 35° C., and after the completion of reaction, the solution is filtered and filter residue is washed to collect the filtrate, and then the filtrate is purified to obtain the branched polyethylene glycol epoxy derivative.

The general formula of the above reaction is as follows:

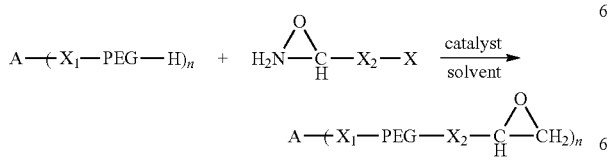

The branched polyethylene glycol epoxy derivative synthesized by the above method has higher purity, and the purity is more than 99% as detected by HPLC. The polyethylene glycol epoxy derivative crosslinking agent with low toxicity, high reactivity and super-hydrophilic property can be used in crosslinking of high-molecular polymers, such as, natural polymer (e.g., natural polysaccharides and proteins) and synthetic polymer (e.g., polyethylene glycols and polyvinyl alcohols).

A further aspect of the present invention further provides a crosslinking agent, the crosslinking agent includes the above branched polyethylene glycol epoxy derivative of the present invention.

A further aspect of the present invention further provides a high-molecular polymer crosslinked by the above branched polyethylene glycol epoxy derivative. The high-molecular polymer may be a natural polymer and/or synthetic polymer.

Specifically, the natural polymer is selected from: one or more of chitin and chitin derivatives (e.g., carboxymethyl chitin and carboxyethyl chitin), chitosan and chitosan derivatives (e.g., carboxymethyl chitosan and carboxyethyl chitosan, etc.), carrageenan and carboxymethyl carrageenan, cellulose derivatives (e.g., carboxymethyl cellulose, hydroxypropyl cellulose, hydroxypropyl methylcellulose, etc.), starch and starch derivatives (e.g., carboxymethyl starch, etc.), sodium alginate, guar gum and carboxymethyl guar gum, collagen, hyaluronic acid and hyalurate (e.g., sodium hyaluronate, potassium hyaluronate, calcium hyaluronate, magnesium hyaluronate, zinc hyaluronate, cobalt hyaluronate, tetrabutylammonium hyaluronate, etc.).

The synthetic polymer is selected from any one or more of the group consisting of: polyvinylpyrrolidone, polyethylene glycol, polyethylene oxide, polyvinyl alcohol, polyvinyl acetate, polylactic acid, polyglycolic acid, polyacrylic acid, polyacrylamide, polytetrahydrofuran, polybutylene oxide, polyoxetane, polymaleic anhydride, poly (2-hydroxyethylmethacrylate), polypropylene glycol, polycaprolactone, and derivatives thereof; in a preferred embodiment of the present invention, the natural polymer is hyaluronic acid or hyalurate; specifically, the hyalurate is selected from: one or any mixture of sodium hyaluronate, potassium hyaluronate, calcium hyaluronate, magnesium hyaluronate, zinc hyaluronate, cobalt hyaluronate and tetrabutylammonium hyaluronate.

In a more preferred embodiment of the present invention, the hyalurate is sodium hyaluronate.

In a preferred embodiment of the present invention, the crosslinked high-molecular polymer is crosslinked sodium hyaluronate.

In one embodiment of the present invention, molecular weight of the sodium hyaluronate is 50,000-3000,000 Dalton, specifically 50,000-1000,000 Dalton (e.g., 50,000, 100,000, 200,000, 300,000, 400,000, 500,000, 600,000, 700,000, 800,000, 900,000, or 1000,000 Dalton or 1000,000-3000,000 Dalton (e.g., 1000,000, 1500,000, 2000,000, 2500,000, 3000,000 Dalton).

A further aspect of the present invention further provides a gel, and the gel contains the above crosslinked high-molecular polymer of the present invention.

In a preferred embodiment of the present invention, the high-molecular polymer is hyaluronic acid or hyalurate in the gel; specifically, the hyalurate is selected from: one or any mixture of sodium hyaluronate, potassium hyaluronate, calcium hyaluronate, magnesium hyaluronate, zinc hyaluronate, cobalt hyaluronate and tetrabutylammonium hyaluronate.

In a preferred embodiment of the present invention, the crosslinked high-molecular polymer is crosslinked sodium hyaluronate.

In one embodiment of the present invention, molecular weight of the sodium hyaluronate is 50,000-3,000,000 Dalton in the gel.

A further aspect of the present invention provides a preparation method of the high-molecular polymer crosslinked by the above branched polyethylene glycol epoxy derivative, including a step of crosslinking the high-molecular polymer with the above branched polyethylene glycol epoxy derivative in alkaline condition.

In one embodiment of the present invention, the crosslinking reaction is conducted in alkaline solution.

In one embodiment of the present invention, the alkaline solution is selected from: one or more of sodium hydroxide, potassium hydroxide and sodium carbonate solution.

In a preferred embodiment of the present invention, the alkaline solution is NaOH aqueous solution with 0.1-10% mass concentration.

In one embodiment of the present invention, the crosslinked high-molecular polymer is crosslinked sodium hyaluronate, and the preparation method includes a step of dissolving the branched polyethylene glycol epoxy derivative into alkaline solution and adding to powdered sodium hyaluronate for reaction with agitation.

In one embodiment of the present invention, molar ratio of the branched polyethylene glycol epoxy derivative to polymer units in hyaluronic acid is 0.01-1:1, specifically, 0.01:1, 0.05:1, 0.1:1, 0.15:1, 0.2:1, 0.25:1, 0.3:1, 0.4:1, 0.5:1, 0.6:1, 0.7:1, 0.8:1, 0.9:1 or 1.0:1, preferably 0.1-0.5:1.

In one embodiment of the present invention, mass ratio of the sodium hyaluronate to alkaline solution is 1:5-30, specifically, 1:5, 1:10, 1:15, 1:20, 1:25 or 1:30.

In one embodiment of the present invention, the reaction temperature is 35-45° C., specifically, 35, 36, 38, 40, 42, 44 or 45° C., preferably 40° C.

In one embodiment of the present invention, molecular weight of the sodium hyaluronate is 50,000-3,000,000 Dalton, specifically 50,000-1,000,000 Dalton (e.g., 50,000, 100,000, 200,000, 300,000, 400,000, 500,000, 600,000, 700,000, 800,000, 900,000, or 1,000,000 Dalton or 1,000,000-3,000,000 Dalton (e.g., 1,000,000, 1,500,000, 2,000,000, 2,500,000, 3,000,000 Dalton).

In one embodiment of the present invention, the preparation method further includes a step of crosslinking agent removal; specifically, the crosslinking agent removal includes the step of neutralizing the above crosslinked products successively and swelling.

In one embodiment of the present invention, the neutralizing the above crosslinked products is that the solution pH is regulated to neutral by adding acid, preferably, the acid is hydrochloric acid, more preferably, hydrochloric acid (concentration=0.1 N-2 N).

In one embodiment of the present invention, the swelling includes: appropriate amount of PBS buffer solution is added to swell crosslinked products.

In one embodiment of the present invention, the step of crosslinking agent removal further includes dialysis.

The present invention further provides a preparation method of the above gel, including the steps of the preparation method of the above crosslinked high-molecular polymer.

In one embodiment of the present invention, the preparation method further includes sieving, loading and sterilization.

In one embodiment of the present invention, the sterilization is conducted in steam for 8-25 min at 121° C.-125° C.

In a preferred embodiment of the present invention, the preparation method of the above gel includes the following specific steps:

step I: the branched polyethylene glycol epoxy derivative is dissolved into alkaline solution and added to powdered sodium hyaluronate for reacting at 35-45° C., preferably 40° C. to form the crosslinked sodium hyaluronate gel;

step II: an acid is added to neutralize the gel;

step III: an appropriate amount of PBS buffer solution is added to swell the gel;

step IV: the gel is dialyzed repeatedly to remove the residual small-molecular crosslinking agent in the gel;

step V: it is sieved by a standard sieve;

step VI: the gel particles collected in step VI are loaded in a sterilized disposable syringe for sterilization in 121° C.-125° C. steam for 8-25 min, so as to obtain the modified sodium hyaluronate gel for injection.

A further aspect of the present invention further provides an application of the above branched polyethylene glycol derivative in the preparation of the above crosslinking agent, crosslinked high-molecular polymer and gel.

In one embodiment of the present invention, the crosslinked high-molecular polymer is crosslinked hyaluronic acid or crosslinked hyalurate.

In a preferred embodiment of the present invention, the crosslinked high-molecular polymer is crosslinked sodium hyaluronate.

In one embodiment of the present invention, the gel is a gel containing crosslinked sodium hyaluronate.

A further aspect of the present invention further provides an application of the above crosslinking agent in the preparation of crosslinked high-molecular polymer or gel.

In one embodiment of the present invention, the crosslinked high-molecular polymer is crosslinked hyaluronic acid or crosslinked hyalurate.

In a preferred embodiment of the present invention, the crosslinked high-molecular polymer is crosslinked sodium hyaluronate.

In one embodiment of the present invention, the gel is a gel containing crosslinked sodium hyaluronate.

A further aspect of the present invention further provides an application of the above crosslinked high-molecular polymer or the above gel in the preparation of products for medicine, cosmetic plastic surgery, cosmetics or health-care food.

In one embodiment of the present invention, the crosslinked high-molecular polymer is crosslinked hyaluronic acid or crosslinked hyalurate.

In a preferred embodiment of the present invention, the crosslinked high-molecular polymer is crosslinked sodium hyaluronate.

In one embodiment of the present invention, the gel is a gel containing crosslinked sodium hyaluronate.

In one embodiment of the present invention, the product for cosmetic plastic surgery is a soft tissue filler.

In one embodiment of the present invention, the product for medicine comprises a postoperative anti-blocking agent, drug carrier and other drugs for preventing and/or treating diseases.

A further aspect of the present invention provides a soft tissue filler, including the above crosslinked high-molecular polymer or gel.

In one embodiment of the present invention, the crosslinked high-molecular polymer is crosslinked hyaluronic acid or crosslinked hyalurate.

In a preferred embodiment of the present invention, the crosslinked high-molecular polymer is crosslinked sodium hyaluronate.

In one embodiment of the present invention, the gel is a gel containing crosslinked sodium hyaluronate.

Beneficial effects of the crosslinked sodium hyaluronate prepared by the novel crosslinking agent of the present invention are as follows: the crosslinking agent used in the crosslinked sodium hyaluronate gel prepared by the present invention is a polyethylene glycol epoxy derivative. Due to the existence of multiple ether bonds in the molecule of the crosslinking agent, there are more hydrogen bonds in the gel system, thus enhancing the gel stability; meanwhile, due to the particularity of the space structure of the branched polyethylene glycol epoxy derivative, the gel prepared has a more complex winding structure in its space and better stability. Moreover, the branched polyethylene glycol epoxy derivative involved in the present invention is a compound with single molecular weight, and the gel prepared has better batch stability.

The present invention is integrated with gelatinizing and impurity removal technology of crosslinked sodium hyaluronate to prepare the modified sodium hyaluronate gel for injection with low toxicity, low residue, squeezing force, good shaping property, good enzyme resistance and long retention time in vivo; the sodium hyaluronate crosslinked by branched polyethylene glycol epoxy derivative of the present invention has a more compact structure, and the crosslinked sodium hyaluronate gel has more superior stability.

DETAILED DESCRIPTION OF THE EMBODIMENTS

The technical solution of the present invention will be described clearly and completely hereafter with reference to embodiments of the present invention, apparently, embodiments described herein are only a part of embodiments of the present invention, and are not all of embodiments thereof. Based on the embodiments of the present invention, all other embodiments obtained by those skilled in the art without any creative efforts are within the protection scope of the present invention.

Embodiment 1: Synthesis of 4-Armed Dodecaethylene Glycol Tetraglycidyl Ether (Ia)

Synthesis of 4-armed dodecaethylene glycol tetraglycidyl ether with the following structure:

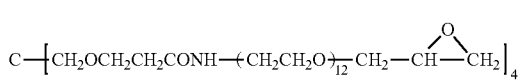

Ia 4-armed dodecaethylene glycol (C—[CH$_2$OCH$_2$CH$_2$CONH—(CH$_2$CH$_2$O)$_{12}$H]$_4$, 0.1 mol), tetrahydrofuran (THF, 100 mL) and potassium hydroxide (0.8 mol) were added to a three-port bottle for agitation in water bath, and then epoxy chloropropane (ECH, 1.2 mol) was dropwise added to the reaction system for reaction at room temperature over night, where the reaction temperature was controlled within 35° C. At the end of the reaction, the reaction liquid was filtered, filter residue was washed by dichloromethane, then filtrate was collected to remove dichloromethane by rotary evaporation, thus obtaining a crude product. The crude product was separated by a silicagel column to obtain purified 4-armed dodecaethylene glycol tetraglycidyl ether.

$^1$H-NMR (DMSO-d$_6$): 2.26-2.30 (m, 8H), 2.54-2.55 (m, 4H), 2.72-2.73 (m, 4H), 3.09-3.10 (m, 4H), 3.17-3.28 (m, 20H), 3.35-3.64 (m, 192H), 3.70-3.71 (m, 4H), 7.88-7.92 (t, 4H);

MALDI-TOF (2780.3, M+Na).

Embodiment 2: Synthesis of 4-Armed PEG24 Tetraglycidyl Ether (Ib)

Synthesis of 4-armed PEG24 tetraglycidyl ether with the following structure:

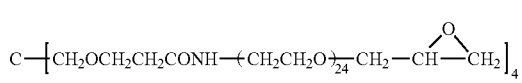

Ib 4-armed PEG24 (C—[CH$_2$OCH$_2$CH$_2$CONH—(CH$_2$CH$_2$O)$_{12}$H]$_4$, 0.1 mol), tetrahydrofuran (THF, 100 mL) and potassium hydroxide (0.8 mol) were added to a three-port bottle for stirring in water bath, and then epoxy chloropropane (ECH, 1.2 mol) was dropwise added to the reaction system for reaction at room temperature over night, where the reaction temperature was controlled within 35° C. At the end of the reaction, the reaction liquid was filtered, filter residue was washed by dichloromethane, then filtrate was collected to remove dichloromethane by rotary evaporation, thus obtaining a crude product. The crude product was separated by a silicagel column to obtain purified 4-armed PEG24 tetraglycidyl ether.

$^1$H-NMR (DMSO-d$_6$): 2.26-2.30 (m, 8H), 2.54-2.55 (m, 4H), 2.72-2.73 (m, 4H), 3.09-3.10 (m, 4H), 3.17-3.28 (m, 20H), 3.35-3.64 (m, 384H), 3.70-3.71 (m, 4H), 7.88-7.92 (t, 4H);

MALDI-TOF (4665.9, M+Na).

Embodiment 3: Synthesis of 8-Armed Tetraethylene Glycol Octaglycidyl Ether (Ic)

Synthesis of 8-armed tetraethylene glycol octaglycidyl ether with the following structure:

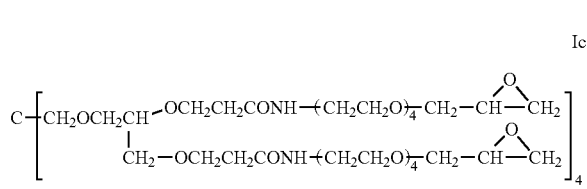

Ic 8-armed tetra ethylene glycol

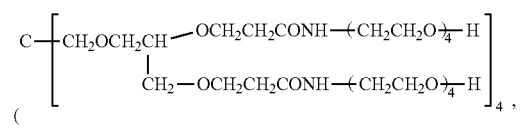

0.1 mol), tetrahydrofuran (THF, 100 mL) and potassium hydroxide (1.6 mol) were added to a three-port bottle for stirring in water bath, and then epoxy chloropropane (ECH, 2.4 mol) was dropwise added to the reaction system for reaction at room temperature over night, where the reaction temperature was controlled within 35° C. At the end of the reaction, the reaction liquid was filtered, filter residue was washed by dichloromethane, then filtrate was collected to remove dichloromethane by rotary evaporation, thus obtaining a crude product. The crude product was separated by a silicagel column to obtain purified 8-armed tetraethylene glycol octaglycidyl ether.

$^1$H-NMR (DMSO-d$_6$): 2.27-2.33 (m, 16H), 2.54-2.55 (m, 8H), 2.72-2.73 (m, 8H), 3.09-3.10 (m, 8H), 3.16-3.26 (m, 24H), 3.28-3.44 (m, 24H), 3.48-3.50 (m, 116H), 3.55-3.60 (m, 8H), 3.66-3.71 (m, 16H), 7.87-7.90 (t, 8H);

MALDI-TOF (2880.8, M+Na).

Embodiment 4: Synthesis of 8-Armed Dodecaethylene Glycol Octaglycidyl Ether (Id)

Synthesis of 8-armed dodecaethylene glycol octaglycidyl ether with the following structure:

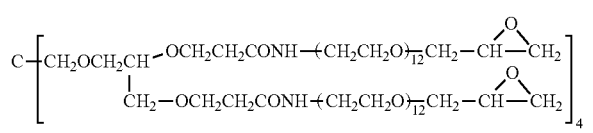

8-armed dodecaethylene glycol

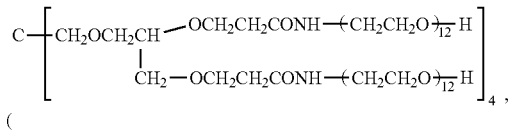

0.1 mol), tetrahydrofuran (THF, 100 mL) and potassium hydroxide (1.6 mol) were added to a three-port bottle for stirring in water bath, and then epoxy chloropropane (ECH, 2.4 mol) was dropwise added to the reaction system for reaction at room temperature over night, where the reaction temperature was controlled within 35° C. At the end of the reaction, the reaction liquid was filtered, filter residue was washed by dichloromethane, then filtrate was collected to remove dichloromethane by rotary evaporation, thus obtaining a crude product. The crude product was separated by a silicagel column to obtain purified 8-armed dodecaethylene glycol octaglycidyl ether.

$^1$H-NMR (DMSO-d$_6$): 2.28-2.33 (m, 16H), 2.54-2.55 (m, 8H), 2.72-2.73 (m, 8H), 3.09-3.10 (m, 8H), 3.16-3.27 (m, 24H), 3.29-3.44 (m, 24H), 3.47-3.50 (m, 372H), 3.55-3.60 (m, 8H), 3.66-3.71 (m, 16H), 7.87-7.90 (t, 8H);

MALDI-TOF (5698.4, M+Na).

Embodiment 5: 4-Armed Dodecaethylene Glycol Tetraglycidyl Ether Crosslinked Sodium Hyaluronate Gel (IIa)

The crosslinking agent, 4-armed dodecaethylene glycol tetraglycidyl ether (0.2 mol, prepared by Embodiment 1) was dissolved into NaOH solution and added powdered sodium hyaluronate (1 mol polymer unit) for reaction with agitation at 40° C. to form crosslinked sodium hyaluronate gel; secondly, an appropriate amount of hydrochloric acid was added to the gel to adjust pH=7.0, then an appropriate amount of PBS buffer solution to swell the gel; afterwards, the gel was sieved by a standard pharmacopeia sieve to collect gel particles, finally, the gel was repeatedly dialyzed, sieved by the standard pharmacopeia sieve, filled and sterilized by steam to obtain the modified sodium hyaluronate gel for injection.

Embodiment 6: 4-Armed PEG24 Tetraglycidyl Ether Crosslinked Sodium Hyaluronate Gel (IIb)

The crosslinking agent, 4-armed PEG24 tetraglycidyl ether (0.2 mol, prepared by Embodiment 2) was dissolved into NaOH solution and added powdered sodium hyaluronate (1 mol polymer unit) for reaction with agitation at 40° C. to form crosslinked sodium hyaluronate gel; secondly, an appropriate amount of hydrochloric acid was added to the gel to adjust pH=7.0, then an appropriate amount of PBS buffer solution to swell the gel; afterwards, the gel was sieved by a standard pharmacopeia sieve to collect gel particles, finally, the gel was repeatedly dialyzed, sieved by the standard pharmacopeia sieve, loaded and sterilized by steam to obtain the modified sodium hyaluronate gel for injection.

Embodiment 7: 8-Armed Tetraethylene Glycol Octaglycidyl Ether Crosslinked Sodium Hyaluronate Gel (IIc)

The crosslinking agent, 8-armed tetraethylene glycol octaglycidyl ether (0.2 mol, prepared by Embodiment 3) was dissolved into NaOH solution and added powdered sodium hyaluronate (1 mol polymer unit) for reaction with agitation at 40° C. to form crosslinked sodium hyaluronate gel; secondly, an appropriate amount of hydrochloric acid was added to the gel to adjust pH=7.0, then an appropriate amount of PBS buffer solution to swell the gel; afterwards, the gel was sieved by a standard pharmacopeia sieve to collect gel particles, finally, the gel was repeatedly dialyzed, sieved by the standard pharmacopeia sieve, loaded and sterilized by steam to obtain the modified sodium hyaluronate gel for injection.

Embodiment 8: 8-Armed Dodecaethylene Glycol Octaglycidyl Ether Crosslinked Sodium Hyaluronate Gel (IId)

The crosslinking agent, 8-armed dodecaethylene glycol octaglycidyl ether (0.2 mol, prepared by Embodiment 4) was dissolved into NaOH solution and added powdered sodium hyaluronate (1 mol polymer unit) for reaction with agitation at 40° C. to form crosslinked sodium hyaluronate gel; secondly, an appropriate amount of hydrochloric acid was added to the gel to adjust pH=7.0, then an appropriate amount of PBS buffer solution to swell the gel; afterwards, the gel was sieved by a standard pharmacopeia sieve to collect gel particles, finally, the gel was repeatedly dialyzed, sieved by the standard pharmacopeia sieve, loaded and sterilized by steam to obtain the modified sodium hyaluronate gel for injection.

Embodiment 9: In-Vitro Stability Test

The crosslinked sodium hyaluronate gel was degraded by hyaluronidase solution to test the in-vitro stability of the gel.

Test Method:

0.5 g crosslinked sodium hyaluronate gel was taken and added to 2 mL 300 U/ml hyaluronidase solution for degradation at 37° C. for 40 h, PBS was added to 5 mL, 1 ml solution was taken, added 4 mL absolute ethyl alcohol and centrifuged for 15 min at 10000 r/min, 2 mL supernatant was taken and adjusted to the volume of 5 mL with PBS, to produce solution A; another 0.5 g crosslinked sodium hyaluronate gel was taken and added 10 mL 0.5 mol/L sulfuric acid solution, hydrolyzed for 15 min in boiling water bath, the solution was added water to 100 mL, to produce solution B. 1 mL solution A and 1 mL B was respectively taken to test the content of glucuronic acid by modified carbazole developing process. In-vitro enzymatic degradation resistance of the gel is denoted by coefficient R, R=1-0.625A/B, in which, A is the content of glucuronic acid in solution A, and B is the content of glucuronic acid in solution B. The higher the R, the better the in-vitro enzymatic degradation resistance is, and the more stable is the crosslinked gel. Test results were as shown in table 1.

TABLE 1

Test results of in-vitro enzymolysis stability of the crosslinked sodium hyaluronate gel

| Test group | IIa | IIb | IIc | IId | BDDE-HA |
|---|---|---|---|---|---|
| Coefficient of enzymatic degradation resistance | 91% | 88% | 81% | 89% | 71% |

Test results show that compared with conventional cross-linking agents, e.g., BDDE crosslinked sodium hyaluronate gel, the branched polyethylene glycol epoxy derivative crosslinked sodium hyaluronate gel has better in-vitro stability.

What is described above are merely preferred embodiments of the present invention, and are not to limit the present invention; any modification and equivalent replacement, etc. within the spirit and principle of the present invention shall be covered in the protection scope of the present invention.

What is claimed is:

1. A branched polyethylene glycol epoxy derivative, having the following structure:

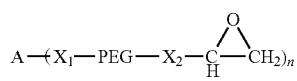
(I)

wherein, A is a core structure, which has the following structure:

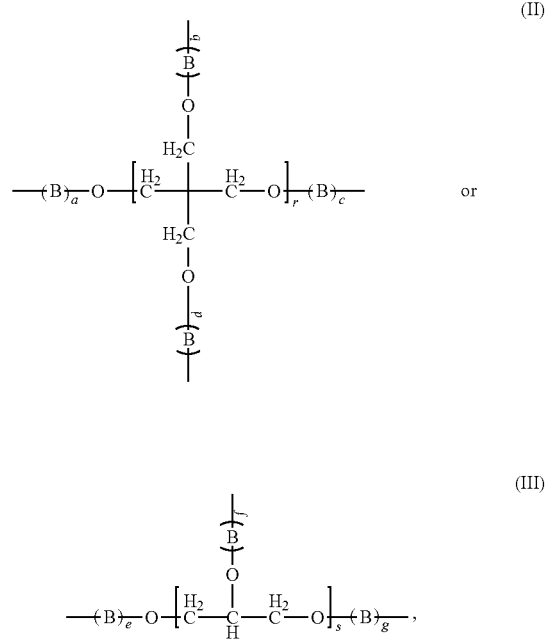

wherein, B has the following structure:

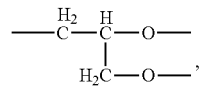

r is an integer of 1-5, a, b, c and d are integers, independently selected from 0 and 1, s is an integer of 1-5, e, f and g are integers, independently selected from 0 and 1;

$X_1$ and $X_2$ are linking groups, wherein $X_1$ is —$CH_2CH_2CONH$—, and $X_2$ is selected from any one or a combination of two or more of the group consisting of: —$CH_2$—, —$CH_2CH_2$—, —$CH_2CH_2CH_2$—, —$CH_2CONH$—, —$CH_2CH_2CONH$—, —$CH_2CONHCH_2$—, —$CH_2CONHCH_2CH_2$—, —$CH_2CH_2CONHCH_2CH_2$—, —$CH_2CH_2NHCOCH_2$— and —$CH_2CH_2NHCOCH_2CH_2$—;

PEG has the following structure: —$(CH_2CH_2O)_m$—, m is an integer of 4-200, n is an integer of 3-24, and the branched polyethylene glycol epoxy derivative is a compound with single molecular weight.

2. The derivative according to claim 1, wherein r is an integer of 1, 2 or 3, s is an integer of 1, 2 or 3.

3. The derivative according to claim 1, wherein the A is selected from the following structures:

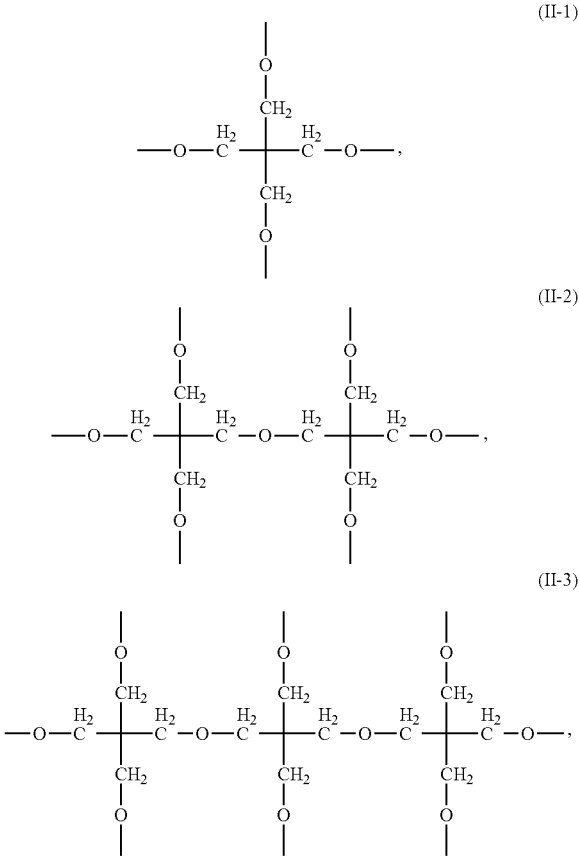
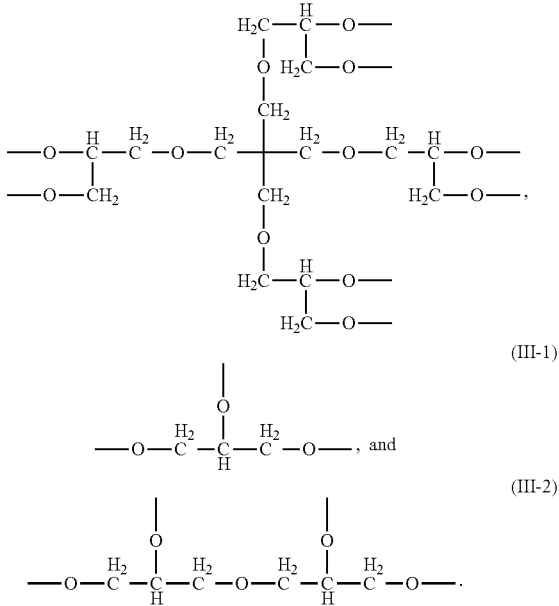
4. The derivative according to claim 1, wherein the m is an integer of 4-100.
5. The derivative according to claim 1, wherein the $X_2$ is —$CH_2$—.
6. The derivative according to claim 5, wherein the branched polyethylene glycol epoxy derivative has the following structure:
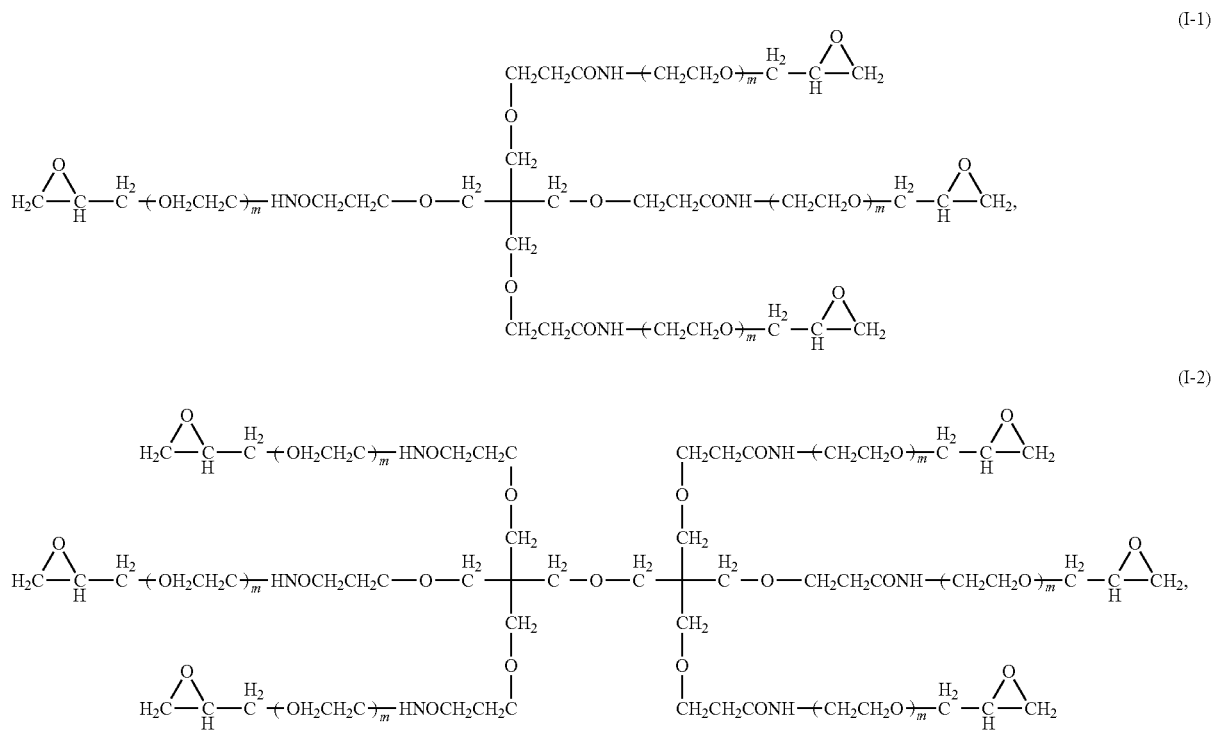

(I-3)
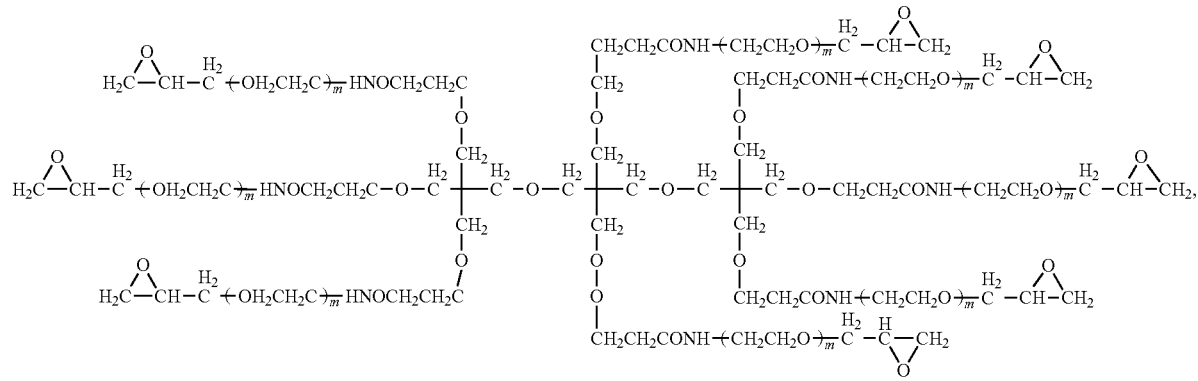
(I-4)
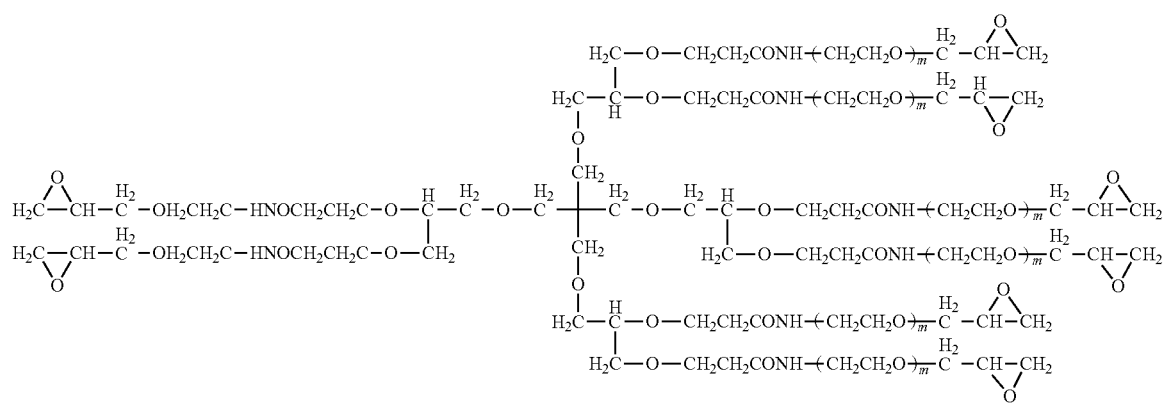
(I-5)
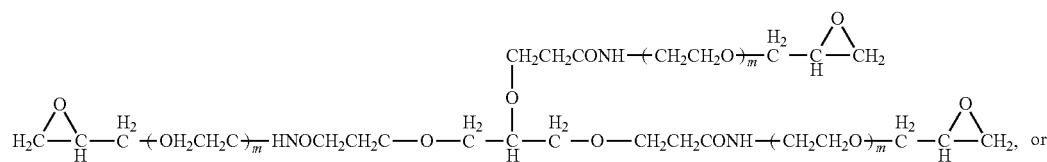
(I-6)
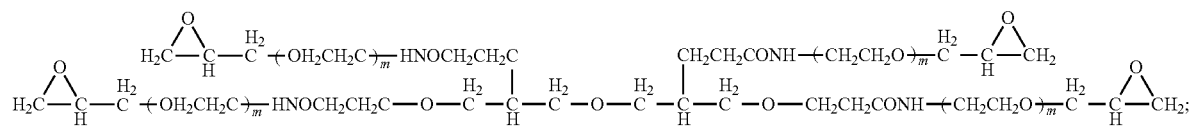
the m is 4, 12 or 24.
7. A preparation method of the branched polyethylene glycol epoxy derivative according to claim 1, wherein the method comprises a step of catalyzing
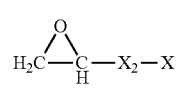
and branched polyethylene glycol $A\text{-}(X_1\text{-PEG-H})_n$ for reaction via a catalyst in solvent,
wherein, A is a core structure, which has the following structure:
(II)
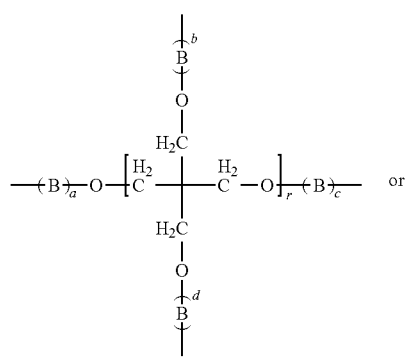

-continued

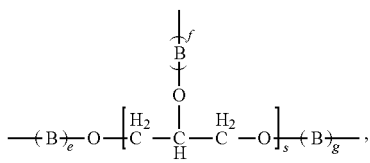
(III)

wherein, B has the following structure:

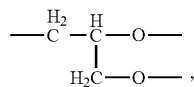

r is an integer of 1-5,
a, b, c and d are integers, independently selected from 0 and 1,
s is an integer of 1-5,
e, f and g are integers, independently selected from 0 and 1,
$X_1$ and $X_2$ are linking groups, wherein $X_1$ is —CH$_2$CH$_2$CONH—, and $X_2$ is selected from any one or a combination of two or more of the group consisting of: —CH$_2$—, —CH$_2$CH$_2$—, —CH$_2$CH$_2$CH$_2$—, —CH$_2$CONH—, —CH$_2$CH$_2$CONH—, —CH$_2$CONHCH$_2$—, —CH$_2$CONHCH$_2$CH$_2$—, —CH$_2$CH$_2$CONHCH$_2$CH$_2$—, —CH$_2$CH$_2$NHCOCH$_2$— and —CH$_2$CH$_2$NHCOCH$_2$CH$_2$—;
—X is a leaving group,
PEG has the following structure: —(CH$_2$CH$_2$O)$_m$—, m is an integer of 4-200,
n is an integer of 3-24,
the catalyst is a base catalyst.

8. A crosslinking agent, wherein the crosslinking agent comprises the branched polyethylene glycol epoxy derivative according to claim 1.

9. A high-molecular polymer crosslinked by the branched polyethylene glycol epoxy derivative according to claim 1, wherein the molecular weight of the high-molecular polymer is 50,000-3000,000 Dalton.

10. The crosslinked high-molecular polymer according to claim 9, wherein the high-molecular polymer is a natural polymer and/or synthetic polymer;
the polymer is selected from: one or more of chitin and chitin derivatives, chitosan and chitosan derivatives, carrageenan and carboxymethyl carrageenan, cellulose derivatives, starch and starch derivatives, sodium alginate, guar gum and carboxymethyl guar gum, collagen, hyaluronic acid and hyalurate; and/or,
the synthetic polymer is selected from: one or more of polyvinylpyrrolidone, polyethylene glycol, polyethylene oxide, polyvinyl alcohol, polyvinyl acetate, polylactic acid, polyglycolic acid, polyacrylic acid, polyacrylamide, polytetrahydrofuran, polyepoxybutane, polyoxetane, polymaleic anhydride, poly (2-hydroxyethylmethacrylate), polypropylene glycol, polycaprolactone and derivatives thereof.

11. The crosslinked high-molecular polymer according to claim 9, wherein the crosslinked high-molecular polymer is crosslinked sodium hyaluronate.

12. A preparation method of the crosslinked high-molecular polymer according to claim 9, comprising a step of crosslinking the high-molecular polymer with the branched polyethylene glycol epoxy derivative according to claim 1 in alkaline condition.

13. The preparation method according to claim 12, wherein the crosslinked high-molecular polymer is crosslinked sodium hyaluronate.

14. A gel, wherein the gel comprises the crosslinked high-molecular polymer according to claim 9.

15. A method for preparing a product for medicine, cosmetic plastic surgery, cosmetics or health-care food, the method comprising the step of preparing the products using the crosslinked high-molecular polymer of claim 9.

16. A soft tissue filler, comprising the crosslinked high-molecular polymer of claim 9.

17. A soft tissue filler, comprising the gel of claim 14.

18. The preparation method according to claim 13, wherein molar ratio of the branched polyethylene glycol epoxy derivative according to any one of claims 1-6 to polymer units in hyaluronic acid is 0.01-1:1; and/or, the reaction temperature is 35-45° C.; and/or, molecular weight of the sodium hyaluronate is 50,000-3000,000 Dalton.

19. A gel according to claim 14, wherein the crosslinked high-molecular polymer is crosslinked sodium hyaluronate.

20. A method according to claim 15, wherein the product for cosmetic plastic surgery is a soft tissue filler; and/or, the product for medicine comprises a postoperative anti-blocking agent, drug carrier and other drugs preventing and/or treating diseases.

* * * * *